United States Patent [19]

Krespan

[11] Patent Number: 5,220,082
[45] Date of Patent: Jun. 15, 1993

[54] PROCESS FOR PRODUCTION OF POLYFLUOROOLEFINS

[75] Inventor: Carl G. Krespan, Wilmington, Del.

[73] Assignee: E. I. Du Pont de Nemours and Company, Wilmington, Del.

[21] Appl. No.: 904,263

[22] Filed: Jun. 25, 1992

Related U.S. Application Data

[60] Division of Ser. No. 776,652, Oct. 4, 1991, Pat. No. 5,162,594, which is a continuation-in-part of Ser. No. 595,839, Oct. 11, 1990, abandoned.

[51] Int. Cl.$^5$ .............................................. C07C 22/02
[52] U.S. Cl. .................................. 570/131; 570/124; 570/132; 570/135
[58] Field of Search ........................ 570/131, 132, 124

[56] References Cited

U.S. PATENT DOCUMENTS

| | | | |
|---|---|---|---|
| 2,480,080 | 8/1949 | Ligett et al. | 570/131 |
| 2,951,096 | 8/1960 | Miller | 570/132 |
| 2,992,279 | 7/1961 | Haszeldine | 570/132 |
| 3,046,261 | 7/1962 | Iserson | 570/132 |
| 3,662,009 | 5/1972 | Hutchinson | 260/653.3 |
| 3,816,552 | 6/1974 | Hartwimmer | 570/131 |
| 4,954,666 | 9/1990 | Bielefeldt et al. | 570/124 |
| 5,017,718 | 5/1991 | Ojims | 570/153 |

FOREIGN PATENT DOCUMENTS

| | | |
|---|---|---|
| 856145 | 11/1952 | Fed. Rep. of Germany . |
| 2048772 | 4/1971 | Fed. Rep. of Germany . |

OTHER PUBLICATIONS

Chemical Abstracts, vol. 112, No. 21, May 21, 1990, Abstract No. 197607p, p. 640.

*Primary Examiner*—Joseph E. Evans
*Attorney, Agent, or Firm*—Barbara C. Siegell

[57] ABSTRACT

This invention concerns a process for the production of polyfluoroolefins by the catalytic addition of polyfluoroallylic fluorides to fluoroethylenes. 1:1 and 1:2 Adducts such as F-pentene-2 and F-heptene-3 can be formed selectively and reduced further to dihydro- or trihydropolyfluoroalkanes, which are useful as HFC cleaning agents.

1 Claim, No Drawings

PROCESS FOR PRODUCTION OF POLYFLUOROOLEFINS

CROSS-REFERENCE TO RELATED APPLICATION

This is a divisional of Ser. No. 07/776,652, filed Oct. 4, 1991, now U.S. Pat. No. 5,162,594 which in turn is a continuation-in-part of Ser. No. 07/595,839, filed Oct. 11, 1990, now abandoned.

BACKGROUND OF THE INVENTION

1. Field of the Invention

This invention concerns a process for the production of polyfluoroolefins by the catalytic addition of polyfluoroallylic fluorides to fluoroethylenes. 1:1 and 1:2 Adducts such as F-pentene-2 and F-heptene-3 can be formed selectively and reduced further to dihydro- or trihydropolyfluoroalkanes, which are useful as HFC cleaning agents. Higher boiling products, e.g., boiling points above 100° C. are useful as solvents and stable liquids, particularly after the double bond has been saturated by hydrogenation, fluorination, or chlorination.

2. Technical Review

Various catalysts for the addition of polyfluoroallylic fluorides to fluoroethylenes are known.

G. G. Belen'kii, E. P. Lur'e, and L. S. German, UDC 66.095.253:547.413, Institute of Heteroorganic Compounds, Academy of Sciences of the USSR, Moscow (1975) use $SbF_5$ as a catalyst for carrying out the alkylation of the fluoro derivatives of ethylene using perfluoropropylene and 2-H-perfluoropropylene.

Chang-Ming Hu, Hui Liu and Ze-Qi Xu, Reactions of Perchlorofluoro Compounds VI. Rearrangement of Higher Perchlorofluoroolefins and Their Reactions with Nucleophiles and Electrophiles, teaches the alkali fluoride ion induced formation of a TFE/HFP adduct.

The present invention employs an aluminum halide to catalyze the addition of an allyl fluoride to fluoroethylene.

SUMMARY OF THE INVENTION

The present invention provides a process for the manufacture of polyfluoroolefins having at least 5 carbon atoms comprising reacting a first polyfluoroolefin of the structure

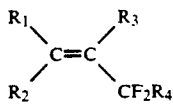

where:
$R_1$ is F, Cl, H or $R_f$;
$R_2$ is F, Cl, H or $R_f$;
$R_3$ is F, Cl, or H;
$R_f$ is a $C_2$ to $C_{12}$ perfluoroalkyl, optionally containing 1H or 1 Cl;
$R_4$ is F or $R_f$ or where $R_4$ together with $R_2$ is $-(CF_2)_n-$; wherein n is 1, 2 or 3;
with a second polyfluoroolefin of structure $R_5CF=CF_2$ and where $R_5$ is F, H, or Cl;

in the presence of a catalyst of the structure $AlX_3$ where X is one or more of F, Cl or Br, provided that X cannot be entirely F.

The invention also concerns olefins of the structures

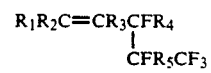

and

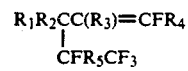

or structures derived therefrom by further "migration" of the double bond. By "migration" is meant a shift in the double bond position in the molecule accompanied by relocation of fluorine.

The invention also concerns olefins of the structures:

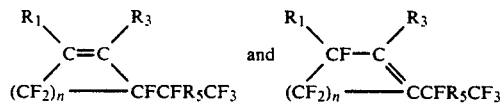

or rearrangement products resulting from a shift of the double bond. (These later olefins result where $R_4$, together with $R_2$ is $-(CF_2)_n-$ in the starting

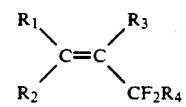

compound) where n is 1, 2 or 3.

DETAILED DESCRIPTION OF THE INVENTION

The equation for the addition reaction which is claimed is as follows (where $R_4$ is F):

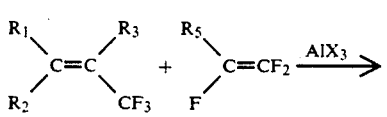

where $R_1$, $R_2$, $R_3$ and $R_5$ are as defined in the Summary of the Invention.

The allylic fluoride may either have the structure shown or be capable of rearranging to that structure by fluorine atom migration in the presence of a catalyst.

The product may also either have the structure shown or a structure resulting from fluorine atom migration. In some cases isomeric products, such as

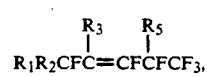

are formed.

The catalyst used is of the structure $AlX_3$, where X is one or more of F, Cl or Br, with a proviso that X cannot be entirely F. Active catalyst can be preformed, as in most examples, or can be formed in situ by partial halogen-F exchange with allylic fluoride, as in Examples 9 and 20. Preferred catalysts are $AlF_xCl_y$ (mixed aluminum halide), where the total number of atoms of halide, x plus y equals 3, where x ranges from 0 to about 2.95 and y ranges from 3 to about 0.05. The $AlF_xCl_y$, where y is greater than 0, may be prepared by pretreating $AlCl_3$ with reactive C—F compounds such as $CF_3CF=CF_2$, $CFCl_3$ or $CHFCl_2$.

Temperatures range from $-20°$ C. to $150°$ C., depending on the reactivity of the reagents but are preferably in the range of $20°$ C. to $85°$ C. Pressures may vary from less than 1 atm to over 50 atm, but a preferred range is from 1 atm to 20 atm. Times for batch reactions may vary from about 5 min. to about 2 days depending on batch size. Times for a continuous reaction may vary from about $\frac{1}{2}$ to 120 min. Times for the reaction vary depending upon the identity of the reactants, the temperature, pressure and amount of catalyst.

The reaction is best conducted in a liquid phase and can be carried out in several modes; batchwise with addition of reactants and catalyst to a reactor cold and warming to reaction temperature; semibatch by injection of one or both reactants optionally containing catalyst into a vessel containing catalyst and or the other reagent at reaction temperature; or continuous by passing the reactants (preferably at least partly liquified, optionally with catalyst) through a reaction zone, which also optionally contains catalyst. The catalyst must be present in the reactant mixture or the reaction zone but may be present in both places. Reactant mole ratios of allylic fluoride (e.g., HFP) to fluoroolefin (e.g., TFE) can vary from 5:1 to 1:50. Ratios in the 5:1 to 1:1 range are generally used when high yields of one to one adducts are desired. Ratios from 1:1 to 1:50 are used when multiple additions of fluoroethylene are desired to form one-to-two and higher adducts, especially when the fluoroolefin is tetrafluoroethylene (TFE). Catalyst loadings in a batch reaction can be from about 0.5 to about 20 wt-%, preferably 2-8 wt-%, of the total charge of reactants.

Solvents are generally not essential, but a liquid phase is useful to facilitate reaction of low-boiling materials that are not condensed under reaction conditions. Solvents are also useful for controlling any initial exotherm when a catalyst, such as aluminum chloride, is used in a large scale reaction. Relatively inert materials which may be used as solvents include hexafluorobenzene, F-n-hexane, $ClCF_2CF_2Cl$, $SO_2ClF$, $CF_3CF_2CHCl_2$, $ClCF_2CF_2CHFCl$, $CF_3CHFCHFCF_2CF_3$, $CF_3CHFCH_2CF_2CF_3$, $CF_3CH_2CHFCF_2CF_3$, $ClCF_2CFCl_2$, $CF_3CCl_3$, $CF_3CCl_2CF_3$, $CF_3CHCl_2$, F-1,2-dimethylcyclobutane, $CCl_2=CCl_2$, $CCl_2=CHCl$, $CF_3CF_2CF_2O[CF(CF_3)CF_2O]_nCHFCF_3$, $(CF_3)_2C=CFCF_2CF_3$, $(CF_3)_2CFCF=CFCF_2$, F-pentene-2, F-heptene-3, F-heptene-2, and $C_nF_{2n}$, where n is 9 or greater. Highly fluorinated olefins are preferred solvents and perfluoroolefins, $C_nF_{2n}$, wherein n is 5 or greater are most preferred. F-pentene-2, for example, is especially preferred for the reaction in which it is also the product, i.e. the condensation of $CF_3CF=CF_2$ with $CF_2=CF_2$, since the reaction mixture can be over 95% $C_5F_{10}$, and therefore easily purified. Selectivity in this procedure is high because $CF_3CF=CF_2$ is much more reactive than $CF_3CF=CFCF_2CF_3$ and, when present, reacts with $CF_2=CF_2$, almost exclusively.

Table I shows various examples and reaction conditions. It should be noted that some of the entries in Table I, in which large excesses of tetrafluoroethylene (TFE) over hexafluoropropene (HFP) were used, resulted in appreciable condensation of TFE with itself to yield even numbers of carbon atoms in product fluoroolefins. Also, as multiple additions of TFE to HFP increase in number, branching in the product olefins becomes more pronounced. Thus, $C_5F_{10}$ and $C_7F_{14}$ are linear products, $C_9F_{18}$ is mainly linear, $C_{11}F_{22}$ and higher have increasing amounts of structures of the type $(R_f)_2C=CFR_f$. These mixtures of high-boiling liquids are converted to even higher boiling, stable liquids by hydrogenation, chlorination or fluorination.

The synthesis described herein can be used to form 1:1 and 1:2 adducts such as F-pentene-2 ($CF_3CF=CFCF_2CF_3$) and F-heptene-3/F-heptene-2 mixtures which can be reduced to form HFC cleaning agents. It can also be used to form higher adducts useful as a source of unreactive solvents, vapor degreasing agents, and stable liquids by chlorination, fluorination or hydrogenation of the double bond.

EXAMPLES

Catalyst Preparation

$AlCl_3 + CF_3CF=CF_2$

A slurry of 100 g (0.75 mol) of $AlCl_3$ (Aldrich, 99.9% pure) in 100 mL of $CCl_4$ was stirred under nitrogen under a $-80°$ C. condenser while 20 g (0.13 mol) of $CF_3CF=CF_2$ was bled in over 1.75 hr. Some unreacted hexafluoropropene, which was present at the end and caused the temperature to drop to $5°$ C., was bled off, and the mixture was warmed to $40°$ C. Another addition of 11 g (0.07 mol) of $CF_3CF=CF_2$ over a 1 hr period resulted in an exotherm to $50°$ C. Continued slow addition at $50°-65°$ C. of 42 g (0.28 mol) of $CF_3CF=CF_2$ finally resulted in persistent reflux of unreacted $CF_3CF=CF_2$. The reaction mixture was transferred to a dry box, where it was filtered. The filter cake was rinsed with $2\times50$ mL of dry $CCl_4$, then dried under vacuum to afford 84.7 g of greenish, free-flowing powder.

Catalyst Preparation

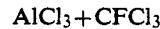
$AlCl_3 + CFCl_3$ 500 g (3.75 mol) of $AlCl_3$ (Aldrich-99% pure) was stirred mechanically under $N_2$ in a r.b. flask fitted with a $-80°$ C. condenser while 1750 mL ($\sim2625$ g, 19 mol) of $CFCl_3$ was added over a 1.5-hr period. Reaction is very exothermic in the early stages, so addition of $CFCl_3$ was slow at first in order to keep the temperature below $65°$ C., then rapid. The resulting suspension was stirred an additional 3 hrs while volatiles ($CF_2Cl_2$) were allowed to escape through the warmed condenser. The condenser was then replaced with a simple stillhead, and most of the $CCl_4$ was distilled under reduced pressure [mainly bp $38°$ C. (200 mm)]. Finally, the last traces of volatiles were removed by warming the residual solid to $30°-35°$ C. at 0.05 mm.

The sealed r.b. flask was transferred to a dry box and unloaded into a Teflon ® FEP bottle; 340 g of rather finely divided yellow-green solid. Portions of the catalyst were weighed out in the dry box as needed and taken out in plastic bottles with pressure-seal caps.

Analysis for fluorine of the products from preparation of this type indicated the composition to be $AlF_{2.9}Cl_{0.1}$, $AlF_xCl_y$; $X = 2.8-2.9$, $Cl = 0.2-0.1$.

EXAMPLE 1

A 400-mL metal tube charged with 16.4 g of fluoridated $AlCl_3$ ($AlCl_3 + CFCl_3$), 100 g (0.5 mol) of 1,1,2-trichloro-3,3,3-trifluoropropene, and 50 g (0.50 mol) of tetrafluoroethene was agitated at 25° C. for 1.5 hr. Fractionation of the liquid product mixture gave 25.4 g (25%) of recovered $CF_3CCl=CCl_2$, then 42.3 g (38% yield)pf F-1,1,2-trichloropentene-1, bp 63°-66° C. (100 mm), identified by IR, NMR and GC/MS. Further fractionation afforded 23.3 g (15%) of an isomeric mixture of F-1,1,2-tetrachloropentene-1 and F-1,1,1-2-tetrachloropentene-2, bp 86°-89° C. (100 mm), identity indicated by IR, NMR and GC/MS. Some higher boiling 2:1 adducts were also present.

The equation for the reaction is shown below:

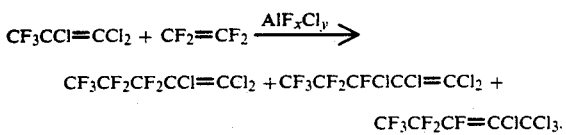

$$CF_3CCl=CCl_2 + CF_2=CF_2 \xrightarrow{AlF_xCl_y}$$
$$CF_3CF_2CF_2CCl=CCl_2 + CF_3CF_2CFClCCl=CCl_2 +$$
$$CF_3CF_2CF=CClCCl_3.$$

EXAMPLE 2

A 400-mL metal tube charged at $-20°$ C. with 8.0 g of $AlF_{2.8}Cl_{0.2}$ (prepared from $AlCl_3 + CFCl_3$), 75 g (0.50 mol) of hexafluoropropene (HEP), and 50 g (0.50 mol) of tetrafluoroethylene (TEE) was shaken for 30 min. while the temperature rose quickly to 20° C. and the pressure dropped to 8 psi. Distillation of the product afforded 88.0 g (70%) of F-pentene-2, b.p. 23°-26° C., identified by IR, NMR and GC/MS. NMR showed the product to be 89% trans-isomer and 11% cis-isomer.

EXAMPLE 3

Reaction of $CF_3CF=CF_2/CF_2=CF_2$ in 1:2 Ratio

A 400-mL metal tube charged cold with 3 g of $AlF_xCl_y$ (fluorinated aluminum chloride catalyst prepared by treating aluminum chloride with $CFCl_3$), 40 g 0.27 mol) of hexafluoropropene, and 50 g (0.50 mol) of tetrafluoroethylene was agitated at 25° C. for 2 hr and at 80° C. for 4 hr. Analysis of the liquid product, 73 g, by GC and MS indicated the presence of 28.2 g (42%) of perfluoro-pentene-2, 42.2 g (48%) of perfluoroheptene isomers, 2.7 g (4%) of perfluorononene isomers, <0.7 g (1%) of $C_{11}F_{22}$ isomers, and traces of higher oligomers, with very small amounts of perfluorohexene and perfluorooctene also detected. Fractionation afforded 21.9 g (32%) of perfluoropentene-2, bp 24°-26° C., followed by 34.1 g (39%) of perfluoroheptenes, bp 69.5°-71° C. Analysis of a center cut, bp 70.9° C., by IR and NMR showed the major component to be trans-perfluoroheptene-3 with only small amounts of other isomers present. Continued fractionation afforded 1.2 g (2%) of perfluorononenes, bp 66°-68° C. (150 mm), shown by IR and NMR to consist mainly of trans-perfluorononene-4 and trans-perfluorononene-3.

EXAMPLE 4

Reaction of $CF_3CF=CF_2/CF_2=CF_2$ in 1:4 Ratio

A 400-mL tube charged cold with 5.0 g of $AlF_xCl_y$, 40 g (0.27 mol) of hexafluoropropene, and 50 g (0.50 mol) of tetrafluoroethylene was shaken at 25° C. for 30 min. while the pressure dropped to 0 psi. Another 50 g (0.50 mol) of tetrafluoroethylene was added, and the mixture was agitated for 4 hr at 25° C. while the pressure again fell to 0 psi. Analysis of the liquid product, 122 g, by GC and MS indicated the presence of 34.5 g (37% yield) of perfluoroheptenes, 59.0 g (49% of perfluorononenes, 22.2 g (15%) of perfluoroundecenes, and 2.0 g (1%) of perfluorotridecenes, with 0.5-1% of perfluoroolefins having even numbers of carbon atoms $C_6F_{12}$, $C_8F_{16}$ and $C_{10}F_{20}$ also detected. Distillation afforded a series of fractions, bp 66° C. (1 atm) to 66° C. (18 mm), which were characterized by GC, IR and NMR analysis. Product boiling at 71°-72° C. was shown to consist of straight-chain trans-perfluoroheptene-3 and trans- and cis-perfluoroheptene-2, with very small amounts of branched olefins (e.g., $CF_3CF_2C(CF_3)=CFCF_2CF_3$) present. Product with bp 74°-80° C. (200 mm) was found to be mainly staight-chain trans-perfluorononene-4 and trans-perfluorononene-3, with perhaps 50% of branched perfluorononenes present in a fraction bp 74° C. (200 mm) dropping to about 5% branched olefins in fractions bp 76°-80° C. (200 mm). The mixed perfluoroundecenes with bp 70°-77° C. (50 mm) were shown to be mainly branched structures of the type $(R_f)_2C=CFR_f$, with linear olefins $R_fCF=CFR_f$ as minor components.

EXAMPLE 20

Reaction of Equimolar $CF_3CF=CF_2$ with $CF_2=CF_2$ with $AlCl_3$ Catalyst in $CCl_2=CCl_2$ Solvent A tube charged cold with 5.0 g of aluminum chloride, 100 mL of tetrachloroethylene, 75 g (0.50 mol) of hexafluoropropene, and 50 g (0.50 mol) of tetrafluoroethylene was shaken at 25°-30° C. for 4 hr while the pressure dropped to 69 psi. The reaction mixture was then heated at 60° C. for 10 hr while the pressure fell to 45 psi. The liquid product, two phases, was distilled to give a foreshot of 4 mL followed by 58.4 g (47%) of perfluoropentene-2, bp 10°-25° C., nearly 100% pure by GC.

Tetrachloroethylene is a preferred solvent because of its availability, relative inertness under reaction conditions, and ease of separation from low boiling 1:1 and 1:2 adducts.

EXAMPLE 21

Addition of $CF_2=CF_2$ to F-Cyclopentene

A 1-L. stirred autoclave was charged with 30 g of $AlF_xCl_y$ and 118 g (0.56 mol) of F-cyclopentene. Tetrafluoroethylene (47.3 g, 0.47 mol) was pressured in and the vessel was heated slowly with stirring to 80° C., where reaction rate was appreciable. Tetrafluoroethylene was added in portions at 80° C. until a total of 114.4 g (1.14 mol) had been added over 14 hr. Reaction was continued another 7 hr. Volatiles obtained by heating the crude reaction product at 100° C. (0.3 mm) were 122.6 g of liquid. Fractionation afforded 96.2 g (55%) of F-1-ethylcyclopentene, bp 64°-66° C., identified by IR and NMR analysis.

EXAMPLE 22

Addition of $CF_2=CF_2$ to $F(CF_2)_4CH=CH(CF_2)_4F$

A metal tube charged with 5 g of $AlF_xCl_y$, 50 g (0.50 mol) of $CF_2=CF_2$, and 139 g (0.30 mol) of $F(CF_2)_4CH=CH(CF_2)_4F$ was shaken at 25° C. for 17 hr. The reaction mixture was filtered and distilled to give 90.5 g (54%) of 1:1 adducts, bp 60°-63° C. (20 mm), identified by GC/MS. The major isomer, about 95% of the total, was shown to be $CF_3CF_2CF_2CF=CHCH(CF_2CF_3)CF_2CF_2CF_2CF_3$ by IR and NMR analysis.

EXAMPLE 23

Use of $CF_3CF=CFCF_2CF_3$ as Solvent

A 400-mL metal tube charged with 5.0 g $AlF_xCl_y$, 49.5 g of $CF_3CF=CFCF_2CF_3$, 75 g (0.50 mol) of $CF_3CF=CF_2$, and 50 g (0.50 mol) of $CF_2=CF_2$ was agitated as it warmed over 0° C. From a peak pressure (115 psig) at 16° C., the pressure fell rapidly to 9 psig, while a slight exotherm carried the temperature to 28° C. before subsiding to 22° C., all in 1 hr. Heating at 60° C. produced no further sign of reaction. GC analysis of the crude product, 169 g, indicated that 110.1 g (88%) of $C_5F_{10}$ had been formed. Only small amounts of by-products such as hexafluoropropene dimer were present.

TABLE I

| Example | Cat (wt. %) | Reactants (molar ratio) | Temp (°C.) (Time (hr.)) | Pressure Range (psig) | Products (% yield) |
|---|---|---|---|---|---|
| 1 | $AlF_xCl_y$ (10) | $CF_3CCl=CCl_2 + CF_2=CF_2$ (1:1) | 25° (1.5) | 166-6 | $F(CF_2)_3CCl=CCl_2$ (38%); $F(CF_2)_2CFClCCl=CCl_2 + F(CF_2)_2CF=CClCCl_3$ (15%) |
| 2 | $AlF_xCl_y$ (6) | $CF_3CF=CF_2 + CF_2=CF_2$ (1:1) | 0-20° (0.5) | down to 8 | 89:11 trans/cis-$F(CF_2)_2CF=CFCF_3$ (70%), trace HFP dimer |
| 3 | $AlF_xCl_y$ (3) | $CF_3CF=CF_2 + CF_2=CF_2$ (1:2) | 25° (2), 80° (4) | 266-68, 96-50 | $F(CF_2)_2CF=CFCF_3$ (32%), $F(CF_2)_3CF=CF(CF_2)_2F$ (39%), $F(CF_2)_5CF=CF(CF_2)_2F + F(CF_2)_4CF=CF(CF_2)_3F +$ others (2%) |
| 4 | $AlF_xCl_y$ (5) | $CF_3CF=CF_2 + CF_2=CF_2$ (1:4) | 11-25° (0.5, 4) (2 TFE additions) | 138-0, 173-0 | $C_7F_{14}$ (37%), $C_9F_{18}$ (49%), $C_{11}F_{22}$ (15%), small amounts other olefins and solid polymer |
| 5 | $AlF_xCl_y$ (3) | $CF_3CF=CFCF_2CF_3 + CF_2=CF_2$ (1:1) Carried out semibatch with TFE added continuously. | 35-40° (4) | 40-60 | $C_7F_{14}$ (78%), $C_9F_{18}$ (6%) |
| 6 | $AlF_xCl_y$ (5) | $CF_3CH=CH_2 - CF_2=CF_2$ (1:1) | 25° (2), 60° (4) | 230-400 | $F(CF_2)_3CH=CH_2$ (low, mainly $CF_3CH=CH_2$ dimers |
| 7 | $AlF_xCl_y$ (4) | 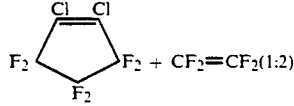 | 80° (3) | 334-19 | 1:1 adducts (36%), 2:1 adducts (32%) |
| 8 | $AlF_xCl_y$ (3) | $CF_3CCl=CClCF_3 + CF_2=CF_2$ (0.8:1) | 80° (2) | 347-34 | $F(CF_2)_3CCl=CClCF_3$ (48%), $F(CF_2)_3CCl=CCl(CF_2)_3F$ (20%) |
| 9 | $AlCl_3$ (2) | $CF_3CF=CF_2 + CF_2=CF_2$ (1:1) | 25° (0.5), 40° (2) | 240, down to 34 | $F(CF_2)_2CF=CFCF_3$ (47), small amts. high boilers |
| 10 | $AlF_xCl_y$ (2) | $CF_3CF=CF_2 + CF_2=CF_2$ (1:1) | 12-26° (4) | 203-35 | $F(CF_2)_2CF=CFCF_3$ (69%) |
| 11 | $AlF_xCl_y$ (4) | $CF_3CH=CF_2 + CF_2=CF_2$ (1:1) | 25° (3.5) | 153-0 | $CF_3CH=CFCF_2CF_3$ (80%), $F(CF_2)_2CF=CH(CF_2)_3F$ (low), plus others |
| 12 | $AlF_xCl_y$ (4) | $CF_3CF=CF_2 + CF_2=CFCl$ (1:1) | 25° (4) | 85-18 | $CF_3CF_2CF=CClCF_3$ (36%), along with $CF_3CF_2CCl=CClCF_3$, $F(CF_2)_3CF=CClCF_2CF_3$, $F(CF_2)_4CCl=CClCF_3$ (18%) and others |
| 13 | $AlF_xCl_y$ (4) | $CF_3CF=CF_2 + CF_2=CF_2$ (1:10) | 4-25° (3, 18) (2 TFE additions) | 152-19, 240-1 | $C_7F_{14}$, $C_9F_{18}$, $C_{11}F_{22}$ and $C_{13}F_{26}$ as major series, $C_8F_{16}$, $C_{10}F_{20}$, and solid polymer also formed |
| 14 | $AlF_xCl_y$ (5) | $CF_3CF=CF_2 + CF_2=CF_2$ (1:30) | 25° (4), 50° (1) (2 TFE additions) | 165-21, 179-44 | $C_6F_{12}$ to $C_{15}F_{30}$ liquids + 12% poly (TFE) |
| 15 | $AlF_xCl_y$ (6) | $C_7F_{14}$ isomers + $CF_2=CF_2$ (1:7) | 25° (10), 50° (6) | 198-0, constant | $C_6F_{12}$ (1%), $C_7F_{14}$ (1%), $C_8F_{16}$ (16%), $C_9F_{18}$ (32%), $C_{10}F_{20}$ (16%), $C_{11}F_{22}$ (30%), $C_{12}F_{24}$ (3%), $C_{13}F_{26}$ (2%) plus polymer |
| 16 | $AlF_xCl_y$ (5) | $(CF_3)_2CFCF=CFCF_3 + CF_2=CF_2$ (1:3) | 10-25° (6) | 160-0 | 1:1 adducts (32%), 2:1 (54%), 3:1 (10%) |
| 17 | $AlF_xCl_y$ (6) | $CF_3CF=CF_2$ ($C_6F_6$ solvent) | 25° (4), 85° (10) | (no readings) | $(CF_3)_2C=CFCF_2CF_3$ (20%), $(CF_3)_2CFCF=CFCF_3$ (2%) |
| 18 | $AlF_xCl_y$ (5) | $(CF_3)_2C=CFCF_2CF_3 + CF_2=CF_2$ (1:3) | 16-25° (8) | 178-0 | $CF_3CF_2CF_2C(CF_3)=CFCF_2CF_3$ (2%), considerable poly (TFE) |
| 19 | $AlBr_3$ (7) | $CF_3CF=CF_2 + CF_2=CF_2$ (1:1) | 25-80° (8) | 220-515 | $C_5F_{10}$ (1%) + $C_7F_{14}$ (1%) |
| 20 | $AlCl_3$ (4) | $CF_2CF=CF_2 + CF_2=CF_2$ (1:1) | 25-30° (4) 60° (10) | see text | $CF_2CF=CFCF_2CF_3$ (47%) |
| 21 | $AlF_xCl_y$ (13) | F-cyclopentene, $CF_2=CF_2$ (1:2) | 80° (21) | no readings | F-1-ethylcyclopentene (55%) |
| 22 | $AlF_xCl_y$ (2.6) | $F(CF_2)_4CH=CH(CF_2)_4F + CF_2=CF_2$ (3:5) | 25° (17) | no readings | $CF_3(CF_2)_2CF=CHCH(CF_2CF_3)(CF_2)_3CF_3 +$ isomers (54%) |
| 23 | $AlF_xCl_y$ (4) | $CF_3CF=CF_2 + CF_2=CF_2$ (1:1) | see text | 115 psi | $C_5F_{10}$ (88%) |

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed:

1. Isomeric compositions of the structures:

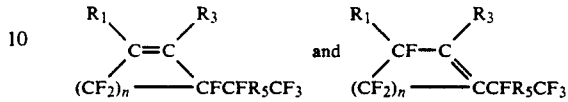

wherein:
$R_1$ is F, Cl, H or $R_f$;
$R_3$ is F, Cl or H;
$R_5$ is F, H or Cl;
n is 1, 2 or 3;
$R_f$ is $C_2$ to $C_{12}$ perfluoroalkyl, optionally containing 1H or 1 Cl.

* * * * *